(12) United States Patent
Kuwano

(10) Patent No.: US 6,905,684 B1
(45) Date of Patent: Jun. 14, 2005

(54) PREVENTIVES AND REMEDIES FOR DIFFUSE LUNG DISEASES

(75) Inventor: Kazuyoshi Kuwano, Fukuoka (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/554,111

(22) PCT Filed: Nov. 9, 1998

(86) PCT No.: PCT/JP98/05025

§ 371 (c)(1),
(2), (4) Date: May 10, 2000

(87) PCT Pub. No.: WO99/24069

PCT Pub. Date: May 20, 1999

(30) Foreign Application Priority Data

Nov. 10, 1997 (JP) .............................. 9-307403
Apr. 30, 1998 (JP) ........................... 10-121298

(51) Int. Cl.⁷ ...................... A61K 39/395; A61K 39/40; A61K 39/42; A61K 39/00; H01L 21/20
(52) U.S. Cl. ............... 424/133.1; 424/130.1; 424/145.1; 424/185.1; 435/326; 436/86; 436/87; 514/1; 530/300; 530/350; 530/385; 530/386; 530/387.1; 530/387.3; 530/388.1; 530/389.2
(58) Field of Search .................... 424/145.1, 185.1, 424/130.1, 133.1; 435/326; 530/389.2, 350, 388.1, 300, 385, 386, 307.1, 387.3; 514/1; 436/86, 87

(56) References Cited

U.S. PATENT DOCUMENTS 6,114,507 A * 9/2000 Shirakawa et al.

FOREIGN PATENT DOCUMENTS

| EP | 0675200 A1 | 10/1995 |
| EP | 0842948 A1 | 5/1998 |
| EP | 0965637 A1 | 12/1999 |
| WO | WO9513293 | 5/1995 |
| WO | WO9702290 | 1/1997 |
| WO | WO9742319 | 11/1997 |

OTHER PUBLICATIONS

Aoshiba et al. The Fas/Fas–ligand system is not requried for bleomycin–induced pulmonary fibrosis in mice. American Journal of Respiratory and Critical Care Medicine 162:659–700, 2000.*
Merriam–Webster's Collegiate Dictionary, tenth edition. 1996.*
Hagimoto et al. Apoptosis and Expression of Fas/Fas Ligand mRNA in Bleomycin–induced Pulmonary Fibrosis in Mice. Am. J. Resp. Cell Mol. Biol. 16:91–101, 1997.*
Hagimoto et al., Am. J. Respir. Cell Mol. Biol., vol. 16, p. 91–101 (1997).
Hagimoto et al., Am. J. Respir. Cell Mol. Biol., vol. 17, p. 272–278 (1997).
Yaekashiwa et al., Am. J. Respir. Crit. CareMed., vol. 156, p. 1937–44 (1997).
Kazufumi et al., Microscopy Research and Technique, vol. 38, pp. 480–487 (1997).
Milik, A.M. et al., J. of Clinical Investigation, vol. 99, No. 5 (1997) pp. 1082–1091.
Program of 17th Meeting Japanese Society of Inflammations, p. 130, No. 16 (1996) and concise English translation.

* cited by examiner

Primary Examiner—Alana M. Harris
(74) Attorney, Agent, or Firm—Birch, Stewart, Kolasch & Birch, LLP

(57) ABSTRACT

Preventives and remedies for diffuse lung diseases whereby apoptosis can be inhibited and thus favorable preventive/therapeutic effects can be established.

These drugs contain apoptosis-inhibiting substances as the active ingredient.

The above apoptosis-inhibiting substances include Fas antagonists and Fas/Fas ligand binding inhibitors such as Fas derivatives and anti-Fas ligand antibodies.

6 Claims, No Drawings

PREVENTIVES AND REMEDIES FOR DIFFUSE LUNG DISEASES

This application is the national phase under 35 U.S.C. § 371 of PCT International Application No. PCT/JP98/05025 which has an International filing date of Nov. 9, 1998, which designated the United States of America.

TECHNICAL FIELD

This invention relates to preventives and remedies for diffuse lung diseases which contain an apoptosis-suppressing substance as their effective component.

BACKGROUND ART

Fas is a cell surface protein which transmits apoptosis signal to the cell, and Fas is recognized by Fas antibody (Yonehara, S. et al., J. Exp. Med., vol. 169, 1747–1756, 1989) which is a monoclonal antibody produced by immunizing a mouse with human fibroblast. Fas gene was recently cloned by Itoh, N. et al., and it was then found out that Fas is a cell membrane protein of about 45 kD, and from the amino acid sequence, it was revealed that Fas is a member of TNF receptor family (Cell, vol. 66, pages 233–243, 1991). Mouse Fas gene was also cloned (Watanabe-Fukunaga, R. et al., J. Immunol., vol. 148, pages 1274–1279, 1992), and the expression of Fas mRNA in thymus, liver, lung, heart, and ovary was confirmed.

Human Fas ligand is a polypeptide which has been reported by Negate et al. to be a biological molecule which induces apoptosis of Fas-expressing cells (Tomohiro Takahashi et al., International Immunology, vol. 6, pages 1567–1574, 1994). Human Fas ligand is a Type II glycoprotein of TNF family with a molecular weight of about 40 kD. As in the case of TNF, human Fas ligand in the human body is estimated to be in the form of a trimer (Masato Tanaka et al., EMBO Journal, vol. 14, pages 1129–1135, 1995). The extracellular domain of the human Fas ligand is highly homologous with the extracellular domain of rat Fas ligand (Takashi Suda et al., Cell, vol. 75, pages 1169–1178, 1993) and mouse Fas ligand (Tomohiro Takahashi et al., Cell, vol. 76, pages 969–976, 1994). The human Fas ligand recognizes not only the human Fas but also the mouse Fas to induce the apoptosis, and vice versa, the rat Fas ligand and the mouse Fas ligand also recognize the human Fas to induce the apoptosis.

Considerable researches have also been done on the mechanism of signal transduction in the cell upon the Fas-mediated apoptosis, and identification and cloning of the factor which interacts with the intracellular domain of the Fas, in particular, the region called "death domain" to transmit or block the signal have been reported. Possibility of the involvement of interleukin-1-converting enzyme (ICE)-related thiol proteases in the signal transduction of the Fas-mediated apoptosis has also been indicated.

Relationship of the apoptosis, in particular, the Fas-mediated apoptosis with various diseases and physiological phenomena has been recently indicated. For example, possibility has been indicated for involvement of abnormal Fas-mediated apoptosis in the death of hepatocytes in viral fulminant hepatitis, in some types of autoimmune diseases, and the like.

Involvement of the Fas/Fas ligand system in functions other than the apoptosis has also been indicated. For example, possibility has been indicated for the Fas/Fas ligand system to act with neutrophils to develop proinflammatory action (Kayagaki, N. et al., Rinshou Meneki (Clinical Immunology), vol. 28, pages 667–675, 1996).

Diffuse lung diseases are a group of diseases including interstitial pneumonia/pulmonary fibrosis and other diseases wherein the lesion expands in diffused manner. Such diseases may be etiologically categorized into cryptogenic diffuse lung diseases, diffuse lung diseases associated with collagen diseases, and phanerogenic diffuse lung diseases. Cryptogenic diffuse lung diseases include idiopathic interstitial pneumonia, and the like. Interstitial pneumonia/pulmonary fibrosis is a disease wherein lung inflammation invites reconstitution in the structure of alveoli and the resulting fibrotic change invites lung shrinkage and consolidation to threaten the life of the patient.

Cause of the fibrotic change of the lung has not been clearly found out. It has been, however, postulated that the fibrotic change of the lung is promoted by the mechanism wherein alveolus macrophage activated by immunocomplex induces accumulation and activation of neutrophils, and the thus induced secretion of cytotoxic oxidant, protease, and myeloperoxidase invites destruction of the pulmonary parenchyma. The alveolus macrophage that has been activated is also postulated to secrete a fibronectin and a growth factor, and the type I collagen secreted from the stimulated fibroblast precipitates in the lung to result in the fibrotic change of lung (Kudou, S., Naika (Internal Medicine), vol. 77, pp. 594–595, 1996; Kokyuki-byogaku (Respiratory Diseases), Oota, Y. et al. ed., Honma, Y. et al., pp. 48–63, 1990, Chugai-Igaku; Cantin, A. et al., Int. Archs Allergy Appl. Immun., vol. 76, suppl. 1, pp. 83–91, 1985).

In the case of the diffuse lung diseases, steroids are presently administered as a symptomatic treatment, and such steroid administration is recognized as a standard therapeutic method. The steroids, however, are well known for their side effects, and delicate care should be taken for the timing, dose and duration of the administration (Konnichi-no Chiryo-Shishin (Therapeutic Guide Today) 1997, Hinohara S. et al. ed.; Idiopathic Fibroid Lung, Nagai S., pp. 300–301, 1997).

An anti-tumor agent, bleomycin is known to be associated with a side effect, and diffuse alveoli disorder is induced in the acute phase and interstitial pneumonia/pulmonary fibrosis is induced in the chronic phase. Animal experiments have demonstrated that administration of bleomycin invites accelerated induction of inflammatory change, and correspondingly, enhanced increase of the fibroblasts and the extracellular matrix and the subsequent increase in the collagen concentration. The fibrotic change then gradually extends to interstitium, pleura, and the areas surrounding the bronchiole. In view of such situation, many investigations are conducted to model the human interstitial pneumonia/pulmonary fibrosis (Sato, S., Kokyu (Respiration), vol. 16, pp. 70–75, 1997).

The inventors of the present invention have reported that administration of the bleomycin into mouse lung by inhalation induces apoptosis of the bronchial and alveolar epithelial cells, as well as expression of Fas in the alveolar epithelial cells and Fas ligand in the infiltrated T cells (Am. J. Respir. Cell. Mol. Biol. vol. 16, pp. 91–101, 1997). The inventors of the present invention have also reported that apoptosis has been recognized in bronchial epithelium and alveolar epithelium in the case of the pulmonary fibrosis associated with idiopathic interstitial pneumonia or collagen diseases; that expression of Fas has been confirmed for bronchial epithelium and alveolar epithelium; and that expression of Fas ligand has been confirmed for the cells collected from bronchoalveolar lavage fluid (Program of 17th Meeting Japanese Society of Inflammations, p. 130, No. 16, 1996).

However, it has been still unknown whether the apoptosis mediated by the Eas and the Fas ligand is directly or indirectly involved in the pathology of the diffuse lung diseases, and no preventive and therapeutic agent for diffuse lung diseases has been known which acts by suppressing such apoptosis.

DISCLOSURE OF THE INVENTION

An object of the present invention is to provide a preventive and therapeutic agent for diffuse lung diseases which acts by the novel mechanism of suppressing apoptosis. More specifically, the present invention provides a preventive and therapeutic agent for diffuse lung diseases which contains an apoptosis-suppressing substance as its effective component and a therapeutic method wherein such agent is used.

The inventors of the present invention have conducted intensive studies on the relation between the diffuse lung diseases and the apoptosis in order to save those suffering from the diffuse lung diseases, and found that pathology is improved in the model of diffuse lung diseases by the apoptosis-suppressing substance. For example, in the model of the bleomycin-induced interstitial pneumonia, histopathology as well as bronchovesicular finding are improved by the anti-Fas antagonist which has the apoptosis-suppressing action. The present invention has been completed on the bases of such finding.

Accordingly, the present invention is directed to a preventive and therapeutic agent as described below.

(1) A preventive and therapeutic agent for diffuse lung diseases containing an apoptosis-suppressing substance as its effective component.

(2) A preventive and therapeutic agent according to (1) wherein said apoptosis-suppressing substance is a Fas antagonist.

(3) A preventive and therapeutic agent according to (1) wherein said apoptosis-suppressing substance is a substance which suppresses binding between Fas and Fas ligand.

(4) A preventive and therapeutic agent according to (1) wherein said apoptosis-suppressing substance is a Fas derivative.

(5) A preventive and therapeutic agent according to (1) wherein said apoptosis-suppressing substance is an anti-Fas ligand antibody.

(6) A preventive and therapeutic agent according to (1) wherein said apoptosis-suppressing substance is a humanized anti-Fas ligand antibody.

(7) A preventive and therapeutic agent according to any one of (1) to (6) wherein said diffuse lung disease is at least one disease selected from the group consisting of cryptogenic interstitial lung diseases, diffuse lung diseases found in collagen diseases or diseases associated with collagen diseases, drug-induced diffuse lung diseases, neoplastic diffuse lung diseases, diffuse lung diseases found in pneumoconiosis or associated with pneumoconiosis, diffuse lung diseases associated with epithelioid cell granuloma, infectious diffuse lung diseases, and diffuse lung diseases caused by other causes.

(8) A preventive and therapeutic agent according to any one or (1) to (6) wherein said diffuse lung disease is the cryptogenic interstitial lung disease.

(9) A preventive and therapeutic agent according to any one of (1) to (6) wherein said diffuse lung disease is the diffuse lung disease found in collagen diseases or diseases associated with collagen diseases.

(10) A preventive and therapeutic agent according to any one of (1) to (6) wherein said diffuse lung disease is the diffuse lung disease found in the drug-induced diffuse lung disease.

(11) A method for preventing and treating diffuse lung diseases by administering an apoptosis-suppressing substance.

BEST MODE FOR CARRYING OUT THE INVENTION

The present invention is hereinafter described in further detail.

The diffuse lung diseases which may be treated by the preventive and therapeutic agent of the present invention include various diseases. Such diseases may be etiologically categorized into cryptogenic interstitial lung diseases; diffuse lung diseases found in collagen diseases and diseases associated with collagen diseases; drug-induced diffuse lung diseases; neoplastic diffuse lung diseases; diffuse lung diseases associated with pneumoconiosis and pneumoconiosis-associated diseases; diffuse lung diseases associated with epithelioid cell granuloma; infectious diffuse lung diseases; and diffuse lung diseases ascribable to other causes. The preventive and therapeutic agent of the present invention is preferably used in cryptogenic interstitial lung diseases, diffuse lung diseases found in collagen diseases and diseases associated with collagen diseases, and drug-induced diffuse lung diseases.

In the case where the cause of the diffuse lung disease or the causal relationship therewith is anticipated, the drug of the present invention can be used as a prophylactic agent at the stage of the causal disease, thereby preventing the diffuse lung disease or aggravation of the condition of the causal disease.

Exemplary cryptogenic interstitial lung diseases include acute idiopathic interstitial pneumonia, chronic idiopathic interstitial pneumonia (idiopathic pulmonary fibrosis), lymphocytic interstitial pneumonia, desquamative interstitial pneumonia, pulmonary angiomyoma associated with diffused hamartoma, Hermansky Pudlak syndrome, histiocytosis X, pulmonary alveolar proteinosis, pulmonary alveolar microlithiasis associated with diffused alveolorrhagia (hemosiderosis), eosinophilic pneumonia(PIE syndrome), and BOOP (bronchiolitis obliterans with organizing pneumonia).

Exemplary diffuse lung diseases found in collagen diseases and diseases associated with collagen diseases include diseases caused by systemic scleroderma, chronic articular rheumatism, dermatomyositis, multiple myositis, systemic lupus erythematosus, multiple arteritis nodosa, mixed connective tissue disease, Sjogren's syndrome, Behcet's syndrome, ankylosing spondylitis, Wegener's granulomatosis, and Churg Strauss syndrome.

Exemplary drug-induced diffuse lung diseases include diseases induced by an antibiotic, antibacterial agent, nitrated hydantoin preparation, sulfa drug, antiarrythmic agent, anti-inflammatory agent, gold preparation, penicillin derivative, interferon, sho-saiko-to, antitumor agent, radiation, and paraquat.

Exemplary neoplastic diffuse lung diseases include bronchioloalveolar carcinoma, lymphangitis carcinornatosa, hematogenous metastasis of cancer to lung, malignant lymphoma, lymphogranulomatosis and Kaposi's sarcoma.

Exemplary pneumonioses and pneumoconiosis-associated diffuse lung diseases include silicosis, asbestosis, chronic berylliosis, siderosis, aluminum pneumoconiosis, and superalloy pneumoconiosis.

Exemplary diffuse lung diseases associated with epithelioid cell granuloma include hypersensitivity pneumonitis and sarcoidosis.

Exemplary infectious diffuse lung diseases include bacterial pneumonia, viral pneumonia, Pneumocystis carinii pneumonia, chlamydial pneumonia, mycoplasma pneumonia, miliary tuberculosis, and mycotic tuberculosis.

Examples of other diffuse lung diseases include high altitude pulmonary edema, diffused pulmonary lesion caused as complication with HIV, and pulmonary lesion caused as complication with infection to HTLV-1.

Also included are diseases wherein lesion expands in diffused manner in lung or wherein diffused shadow is found in lung, adult respiratory distress syndrome (ARDS), inflammatory lung disease, and the like.

In these diseases, a substance which suppresses apoptosis exhibits prophylactic and therapeutic effects by suppressing the apoptosis involved in each disease.

It should be noted that mammals other than human may also be treated by the agent of the present invention although the human is the most important object of the therapy.

The apoptosis-suppressing substance used in the present invention is not limited to any particular type as long as it suppresses or inhibits the apoptosis.

Typical apoptosis-suppressing substances are Fas antagonists and substances which are capable of suppressing the binding between the Fas and the Fas ligand. The substance employed is not limited to any particular type as long as it blocks signal generation by the Fas or transduction of the thus generated signal at some stage to thereby suppress the function or the biological action of the Fas/Fas ligand system, and in particular, the apoptosis. The mechanism of such blockage may be inhibition of the action, function or expression of the Fas ligand or the Fas; interaction with the extracellular domain of the Fas ligand or the Fas; inhibition of the Fas ligand-Fas interaction; affecting the interaction between the cytoplasmic domain of the Fas and the cytoplasmic factor which interacts with the cytoplasmic domain of the Fas; inhibition of the activity of the cytoplasmic factor (for example, ICE-like protease) which is involved in the signal transduction of the Fas-mediated apoptosis, and the like. The apoptosis-suppressing substance may comprise either a high molecular weight protein compound or a low molecular weight compound.

Exemplary apoptosis-suppressing substances include substances which has the activity of suppressing the Fas-mediated apoptosis, such as a Fas derivative; an anti-Fas antibody; an anti-Fas ligand antibody; an antisense oligonucleotide for the gene or its mRNA of the Fas of the Fas ligand; a substance which interacts with the cytoplasmic domain of the Fas; and an ICE inhibitor.

The apoptosis-suppressing substance used in the present invention is preferably a Fas derivative, an anti-Fas antibody, or an anti-Fas ligand antibody which has the action of suppressing the Fas-mediated apoptosis. The Fas and the Fas ligand are preferably those derived from a human source. The anti-Fas antibody and the anti-Fas ligand antibody are preferably an anti-human Fas antibody and an anti-human Fas ligand antibody, respectively, and the anti-Fas ligand antibody is preferably a humanized anti-Fas ligand antibody. A humanized anti-Fas ligand antibody is preferably the one wherein the constant region and the framework region are derived from a human source and the complementarity determining region is derived from a non-human source. The Fas antagonist used in the present invention is preferably the one which suppresses the apoptosis of the Fas-expressing cell in an appropriate assay, for example, in the assay described in International Patent Application Publication No. WO 95/13293.

It should be noted that the references cited herein are incorporated herein by reference.

The antibody used in the present invention may be either a polyclonal antibody or a monoclonal antibody, and the molecular species of the antibody used in the present invention is not particularly limited. The antibody used in the present invention may be either an antibody molecule of normal form or a fragment thereof which is capable of binding to the antigen to inhibit the Fas-mediated apoptosis, for example, Fab, F(ab')$_2$, Fv, or single chain Ev (scfv) which is the Fv of heavy chain linked to the Fv of light chain by an adequate linker to form a single chain. In addition, the antibody used in the present invention may be an immunoglobulin of any class, subclass or isotype. As described above, the antibody used in the present invention is not limited to any particular type as long as it is capable of binding to the Fas ligand or the Fas to inhibit the biological actions of the Fas/Fas ligand system, and in particular, the Fas-mediated apoptosis.

The anti-Fas ligand antibody used in the present invention may be an antibody of any type (either monoclonal or polyclonal) and any origin produced by any appropriate process. The anti-Fas ligand antibody, however, is preferably a monoclonal antibody derived from a mammal. The monoclonal antibody used in the present invention may be produced in any animal species so long as it is a mammal which may be human or non-human. The monoclonal antibody from a mammal other than human may be the one from rabbit or other rodents. The non-limiting preferable examples of such rodents are mouse, rat and hamster, and use of such animals facilitates a convenient production of the monoclonal antibody. Furthermore, the monoclonal antibody is preferably the one which is capable of recognizing the antigen in a conventional immunoprocess such as radio-immunoassay (RIA), enzyme immunoassay (EIA, ELISA), immunofluorescent analysis, or the like, and whose activity of suppressing the apoptosis of the Fas-expressing cell is measurable by an appropriate assay procedure described in International Patent Application Publication No. WO 95/13293, and the like.

Among these, an example of the most preferable anti-Fas ligand antibody is mouse F919-9-18 antibody produced by hybridoma F919-9-18 which was originally deposited on Jun. 22, 1995 in National Institute of Bioscience and Human Technology, Agency of Industrial Science and Technology (1–3, Higashi 1-chome, Tsukuba-shi, Ibaraki-ken, Japan) (Accession No. P-15002) and transferred from the original deposition to the international deposition on May 9, 1996 (Accession No. FERM BP-5535).

The anti-Fas ligand antibody and the anti-Fas antibody used in the present invention may be prepared, for example, by the process described in International Patent Application Publication No. WO 95/13293 and International Patent Application Publication No. WO 95/02290.

When a monoclonal antibody is used in the present invention, such monoclonal antibody may be prepared by the process known in the art, for example, by using Fas, Fas ligand, or a partial peptide thereof for the immunization antigen, immunizing an animal with such antigen in accordance with a conventional process, fusing the resulting immunized cell with a known parent cell by a conventional cell fusion process, and screening for the monoclonal antibody-producing cell by a conventional screening process.

More illustratively, when the immunization antigen is human Fas ligand or its fragment, the nucleotide sequence of the human Fas ligand disclosed in Takahashi, T. (International Immunology, vol. 6, pages 1567–1574, 1994) is used, and this nucleotide sequence is inserted in a known expression vector system to transform an adequate host cell, the desired Fas ligand protein is obtained and purified from the host cell or the supernatant, and the thus obtained purified Fas ligand protein is used for the immunization antigen.

The mammal which is immunized with the immunization antigen is not limited to any particular type, and the mammal may be preferably selected by considering the compatibility with the parent cell used in the cell fusion. Exemplary animals are mouse, rat, hamster, and rabbit.

The immunization of the animal with the immunization antigen may be carried out by a known process. After the immunization and confirmation of the increase of the desired antibody in serum, the immunocytes are collected from the mammal, and subjected to cell fusion. The preferable immunocytes are splenocytes.

The parent cell to be fused with the immunocyte is not limited to any particular type. However, use of a known mammal myeloma cell line, and in particular, a mouse myeloma cell line such as P3(P3x63Ag8.653) (J. Immnol. 123: 1548, 1978) is preferred. The cell fusion of the above-described immunocyte and the myeloma cell may be carried out basically in accordance with known process such as the process of Milstein et al. (Milstein et al., Methods Enzymol. 73: 3–46, 1981).

The hybridoma is then screened for the one producing the target antibody used in the present invention and the monoclonal antibody is produced by known procedures.

The monoclonal antibody is obtained from the thus prepared hybridoma producing the monoclonal antibody used in the present invention by such procedures as cultivating the hybridoma according to the conventional method and obtaining the monoclonal antibody from the supernatant; or transplanting the hybridoma to a mammal compatible with such hybridoma for propagation, and obtaining the monoclonal antibody from the ascite of the mammal. The former process is adapted for producing the monoclonal antibody of high purity, and the latter process is adapted for producing the monoclonal antibody in a large amount.

The monoclonal antibody produced by such process for use in the present invention may be further purified by a known purification means such as salting out, gel filtration, affinity chromatography, and the like.

The monoclonal antibody used in the present invention is not limited to the one produced by using a hybridoma, and may be the one produced by an antibody-producing cell immortalized by EBV and the like or the one produced by a genetic engineering process.

In addition, the anti-Fas ligand antibody or the anti-Fas antibody used in the present invention is preferably a chimeric antibody or a humanized antibody which is an antibody intentionally altered for the purpose of reducing heteroantigenicity to human.

The use of non-human monoclonal antibody such as mouse antibody is associated with defects when it is repeatedly used in treating a human. The first defect is that the mouse monoclonal antibody has a relatively short circulation halflife and when used for human, the mouse monoclonal antibody will not develop other important functional properties of the immunoglobulin.

The second defect is that the non-human monoclonal antibody includes a substantial length of amino acid which is immunogenic when injected into a human patient. More illustratively, it has been demonstrated by a number of studies that, after injection of a foreign antibody, an extremely strong immunoresponce against the antibody may be induced in the patient to essentially nullify the therapeutic effectivity of the antibody after the first treatment. Furthermore, if various mouse monoclonal antibodies or other monoclonal antibodies with the antigenicity against human are developed in future and one or more such non-human antibodies are used for once or for several times, the subsequent administration of such non-human antibody after such initial administration may be nullified due to the crossreactivity even if the subsequent therapy had no relation to the initial therapy. In some case, the non-human antibody administered after the initial administration may even act as a hazardous substance.

An exemplary such chimeric antibody which can be used in the present invention is a chimeric antibody comprising the variable region from the monoclonal antibody of a mammal other than human such as mouse, and the constant region from the human antibody. Such chimeric antibody may be produced by a known chimeric antibody production process, and in particular, by a genetic engineering process.

More preferably, the anti-Fas ligand antibody used in the present invention is a reshaped human antibody wherein complementarity determining region (CDR) of the human antibody is replaced with the complementarity determining region derived from the antibody of a mammal other than human such as mouse. More illustratively, the constant region and the framework region are preferably of human origin, and the complementarity determining region is preferably of non-human origin. A preferable example of the reshaped human antibody (humanized antibody) is humanized antibody having the CDR derived from the murine F919-9-18 antibody, which is disclosed in International Patent Application Publication No. WO 97/02290.

It should be noted that, if necessary, more than one amino acid in the framework (FR) region in the variable region of the antibody may be substituted, deleted or added so that the complementarity determining region of the humanized antibody would form an adequate antigen-binding site.

The humanized antibody used in the present invention may be prepared in accordance with Leachman et al. (Nature 332: 323 (1988) and European Patent Publication No. EP-A-0239400); Queen et al. (Proc. Natl. Acad. Sci. USA 86: 10029 (1989), International Patent Application Publication Nos. WO 90/07861 and WO 92/11018); Co et al. (Proc. Natl. Acad. Sci. USA 88: 2869 (1991)); Co et al. (Nature 351: 501 (1991)); Co et al. (J. Immunol. 148: 1149 (1992)), and the like.

The Fas derivative used in the present invention is not limited to any particular type as long as it is capable of binding at least with the Fas ligand, or capable of inhibiting the Fas licand-mediated apoptosis. The Fas derivative may also be the one which comprises an amino acid sequence of a known Fas that has been arbitrarily mutated at one to several amino acid residues by substitution, deletion, addition or/and insertion, and which inhibits the biological actions of the Fas/Fas ligand system, and in particular, the Fas-mediated apoptosis, with the binding activity to the Fas ligand retained. The Fas derivative may also comprise a mutant of Fas, truncated form of Fas, a chimeric protein, a fusion protein, and a chemically modified Fas. The Fas from which the Fas derivative is derived may be the one derived from any animal species, although use of the Fas of human origin is preferred in consideration of the antigenicity.

Exemplary Fas derivatives are the extracellular domain of a known Fas; a Fas antigen from which the transmembrane domain has been deleted; a chimeric protein of the extracellular domain of a Fas and another protein such as human Fas-Fc (hFas-Fc) which is a chimeric protein of the extracellular domain of human Fas and Fc fragment of human immunoglobulin. The Fas derivative may be the one prepared by any production process by utilizing known sequences and known gene engineering techniques. For example, the process for producing the human Fas-Fc is described in the Examples of International Patent Application Publication No. WO 95/13293.

Desirable Fas derivatives include at least a part or entire portion of Fas antigen extracellular region polypeptide in which at least one amino acid residue is deleted from a group of amino acid residues starting from the N-terminal amino acid residue of the Fas antigen polypeptide to a cysteine residue most close to the N-terminal side (excluding said cysteine residue. For example, a Fas antigen derivative according to the invention is a part or entire portion of Fas antigen extracellular region polypeptide in which at least one amino acid residue is deleted from the 1st to 42nd amino acid residues counting from the N-terminus.

Also included in the Fas derivatives of the present invention are fusion polypeptides made with Fas. Examples of polypeptides for the Fas fusion polypeptides include the entire portion or a part of the constant region of immunoglobulin heavy chain or light chain, the entire portion or a part of the heavy chain constant region excluding its first region (CH1) and the entire portion of the Fc fragment, which may comprise a hinge region, CH2 region and CH3 region in the case of IgG or a part thereof (for example, each of or an optional combination of hinge region, CH2 region, CH3 region and CH4 region).

Another preferable Fas derivative is the Fas having a deletion in its N terminal. Fas derivatives, shFas(nd29)-Fc and shFas(nd29)-hinge, coded in plasmids (pM1304 and pM1317) included in the *E. coli* which were originally deposited on Mar. 14, 1996 in National Institute of Bioscience and Human Technology, Agency of Industrial Science and Technology (1–3, Higashi 1-chome, Tsukuba-shi, Ibaraki-ken, Japan) (Accession Nos. P-15514 and P-15515) and transferred from the original deposition to the international deposition on Mar. 6, 1997 (Accession No. FERM BP-5854 and Accession No. FERM BP-5855) are derivatives including the extracellular domain of the known human Fas from which N terminal sequence of from 1st to 29th amino acid has been deleted, and the shFas(nd29)-Fc and ahFas(nd29)-hinge are highly active and preferable examples of the effective component for the preventive and therapeutic agent of diffuse lung diseases of the present invention.

The Fas derivatives as described above which may be used in the present invention may be confirmed for their activity to bind to the Fas ligand or their activity to suppress the Fas-mediated apoptosis by an appropriate assay method.

The antisense oligonucleotide for the gene or the mRNA of the Fas or the Fas ligand used in the present invention is not limited to any particular sequence as long as it inhibits the expression of the Fas or the Fas ligand, and may be, for example, the antisense oligonucleotide of the Fas ligand disclosed in International Patent Application Publication No. WO 95/13293 (This publication is herein incorporated by reference).

The preventive and therapeutic agent for diffuse lung diseases of the present invention can be used as a therapeutic agent for the patient suffering from the diffuse lung diseases. The preventive and therapeutic agent of the present invention can also be used as a prophylactic agent for those handling a pathogen of the diffuse lung diseases and those therapeutically administered with a pathogen of the diffuse lung diseases for the purpose of treating other diseases, and as an agent for preventing recurrence of the diffuse lung diseases.

The preventive and therapeutic agent for diffuse lung diseases of the present invention is characterized by its inclusion of the apoptosis-suppressing substance as described above. The agent may be in the form of a pharmaceutical composition or kit wherein the apoptosis-suppressing substance is combined as appropriate with at least one pharmaceutical carrier or medium such as sterilized water, physiological saline, a vegetable oil, a mineral oil, a higher alcohol, a higher fatty acid, or a nontoxic organic solvent; and optional additives such as an excipient, a colorant, an emulsifier, a suspending agent, a surfactant, a solubilizer, a nonadsorptive, a stabilizer, a preservative, an antioxidative, a buffer, an isotonizing agent, or a pain relieving agent. The agent may be administered either orally, or parenterally by intravenous, intracoronary, subcutaneous, intramuscular, percutaneous, intrarectal, or topical administration or by inhalation.

Preferably, the preventive and therapeutic agent of the present invention is parenterally administered by either systemic or topical, rapid or continuous administration.

The preventive and therapeutic agent of the present invention may be administered to a human at an appropriate dose which may vary depending on the pathological conditions and the age of the patient as well as the administration route. For example, an adequate divided dose in the range of approximately 0.01 to 100 mg/kg may be selected in the case of systemic administration. The preventive and therapeutic agent for diffuse lung diseases of the present invention, however, is not limited to the administration route and the dose as described above. The agent may be used in combination with other apoptosis-suppressing substance, Fas antagonist, Fas/Fas ligand binding-suppressing reagent, anti-Fas ligand antibody, humanized anti-Fas ligand antibody, or combinations thereof, or in combination with other drugs.

The preventive and therapeutic agent for diffuse lung diseases of the present invention may be formulated into a pharmaceutical preparation in a normal process. For example, an injection may be prepared by dissolving the purified apoptosis-suppressing substance, Fas antagonist, Fas/Fas ligand binding-suppressing reagent, Fas derivative, anti-Fas ligand antibody, or the humanized anti-Fas ligand antibody in a medium such as physiological saline or a buffer and optionally supplementing the solution with an additive such as an anti-adsorptive. The preparation may also be in the form of a lyophilizate which is to be reconstituted before its use, and may contain any of the excipients that are generally used for facilitating the lyodhilization.

The apoptosis-suppressing substance used in the preventive and therapeutic agent for diffuse lung diseases of the present invention exhibits inhibitory effects for organ and tissue disorders in diffuse lung disease models (in particular, in the model of bleomycin-induced pulmonary fibrosis/interstitial lung diseases as shown in Examples). It should be noted that an anti-mouse Fas ligand antibody is used in the demonstration of the inhibitory effects for organ and tissue disorders since the models used in the experiments are mouse models. Equivalent inhibitory effects may be expected for the anti-human Fas ligand antibody when used in human.

It should be noted that the preventive and therapeutic agent for diffuse lung diseases of the present invention exhibits no toxicity as demonstrated in the following Examples, and therefore, it can be used safely. In view of such situation, the preventive and therapeutic agent for diffuse lung diseases of the present invention is expected to exhibit prophylactic, therapeutic, or ameliorating effects for those suffering from the diffuse lung disease.

Next, the present invention is described in further detail by referring to Examples which are given by way of examples and not by way of limiting the scope of the present invention. The abbreviations used in the following description are those commonly used in the art.

The production process and the apoptosis-suppressing activity of the shFas(nd29)-Fc and shFas(nd29)-hinge which are the Fas derivatives contained in the apoptosis-suppressing substance of the present invention are disclosed in Examples 2, 3, 5, 6, and 8 of International Patent Application Publication No. WO 97/42319. The production process and the apoptosis-suppressing activity of the anti-Fas ligand antibody which is contained in the apoptosis-suppressing substance of the present invention are disclosed in International Patent Application Publication No. WO 97/02290.

EXAMPLE 1

Toxicity Study of shFas(nd29)-Fc (1) Test Method

Male, 6 week BDF1 mice (manufactured by Charles River Japan) were administered with shFas(nd29)-Fc at a dose of 10 and 30 mg/kg once in every 2 days for 12 days, namely, for 7 times in total from their tail vein to evaluate the effect of the reagent. The experiment was conducted by dividing the mice into 3 groups each consisting of 3 animals, namely, into the control group, the group administered with 10 mg/kg of the shFas(nd29)-Fc, and the group administered with 30 mg/kg of the shFas(nd29)-Fc. In order to administer an equal amount protein, namely, 30 mg/kg of the protein to each group, the control group was administered with 30 mg/kg of human serum albumin; the group administered with 10 mg/kg of the shFas(nd29)-Fc was administered with 10 mg/kg of the shFas(nd29)-Fc and 20 mg/kg of the human serum albumin; and the group administered with 30 mg/kg of the shFas(nd29)-Fc was administered with 30 mg/kg of the shFas(nd29)-Fc.

The mice were weighed once in every two days from the day of the first administration. The mice were also evaluated for their blood cell count by collecting the blood from their eyeground vein on the 14th day from the day of the first administration. After measuring the blood cell count, plasma was prepared to measure GOT, GPT, and creatinine. Autopsy was also conducted after collecting the blood, and major organs (lung, heart, liver, kidney, spleen, and intestine) were visually inspected for their change in appearance. The blood cell count was measured with an automatic cell counter, K-2000 (Sysmex). GOT, GPT, and creatinine were measured with an autoanalyzer COBASFARA (manufactured by Roche).

(2) Results

No significant effects were recognized in the weight increase, blood cell count, liver (GOT and GPT), kidney (creatinine), and other major organs (findings in visual inspection) in the mice administered with shFas(nd29)-Fc at a dose of 10 and 30 mg/kg once in 2 days for 12 days, namely, for 7 times in total.

EXAMPLE 2

Effects of shFas(nd29)-Fc in Ameliorating the Bleomycin-Induced Pulmonary Fibrosis Model Mouse (1) Preparation of Bleomycin-Induced Pulmonary Fibrosis Model Male, 6 week ICR mice (manufactured by Kyudo K. K.) were used in the experiment. The mice were weighed, intraperitoneally administered with pentobarbital (manufactured by Dinabot Co.) for anesthetization. The mice were then administered with 50 µl solution of bleomycin chloride (manufactured by Nippon Kayaku) dissolved in physiological saline to 4 mg/kg.

(2) Administration of shFas(nd29)-Fc

The mice were administered with shFas(nd29)-Fc by the procedure as described below. Intravenous administration was conducted at day 7 and day 10 after the bleomycin administration at a dose of 50 µg/mouse. Administration of shFas(nd29)-Fc by inhalation to lung was conducted at day 2, 4, 6, and 8 after the bleomycin administration, or at day 2, 4, 6, 8, 10, and 12 after the bleomycin administration by setting 10 ml of 50 µg/ml shFas(nd29)-Fc solution in ultrasonic nebulizer (Omron) and conducting the inhalation for 30 minutes. The control group was administered only with the bleomycin and no shFas(nd29)-Fc.

(3) Histological Evaluation

Thoracotomy was conducted 14 days after the bleomycin administration, and the pulmonary circulation was flushed with saline. The lungs were extirpated, and the extirpated right lung was fixed with 10% formalin solution for 24 hours. The lung was embedded in paraffin, and the section was stained with hematoxylin and eosin. The resulting section was evaluated under light microscope by three evaluators by scoring in accordance with the histological score standard shown in Table 1. The average value is indicated as the histological score.

TABLE 1

| Histological score | Symptom |
| --- | --- |
| 0 | Normal |
| 1 | the inflammatory lesion (lesion infiltrated with inflammatory cell) or fibrosis lesion is less than 25% of the lung parenchyma |
| 2 | the inflammatory lesion (lesion infiltrated with inflammatory cell) or fibrosis lesion is 25% to less than 50% of the lung parenchyma |
| 3 | the inflammatory lesion (lesion infiltrated with inflammatory cell) or fibrosis lesion is 50% or more of the lung parenchyma |

The results are shown in Table 2, below.

TABLE 2

Histological Evaluation at day 14 after the bleomycin administration

| Group | Percentage of animals confirmed to have inflammation and fibrosis | | Histological score |
| --- | --- | --- | --- |
| | n | (%) | average ± S.D. |
| Control | 10 | 100 | 1.73 ± 0.62 |
| shFas(nd29)-Fc 50 µg/mouse, day 7, i.v. | 8 | 38 | 0.33 ± 0.47 |
| shFas(nd29)-Fc 50 µg/mouse, day 10, i.v. | 4 | 25 | 0.08 ± 0.17 |
| shFas(nd29)-Fc 50 µg/ml day 2, 4, 6, 8, 10 and 12, inhalation | 8 | 75 | 0.92 ± 1.00 |
| shFas(nd29)-Fc 50 µg/ml day 2, 4, 6 and 8, inhalation | 4 | 100 | 1.50 ± 0.58 |

(4) Bronchoalveolar Lavage

The mice were anesthetized by intraperitoneally injecting pentobarbital at 14 days after the bleomycin administration. The lung was exposed and tracheal tube was inserted. Bronchoalveolar lavage was performed through the cannulated tube with 5 ml of saline at room temperature. The recovered fluid was filtered through a metal mesh to remove mucus. The cells in the alveolar lavage fluid was calculated on a hemocytometer. The number of macrophage, lymphocyte, neutrophil, and acidophil was calculated by measuring the percentage of each type of cells in 100 cells stained with Diff-Quik (Baxter Diagnostics), and multiplying the results by the total number of cells in the bronchoalveolar lavage fluid.

The results of the bronchoalveolar lavage fluid analysis are shown in Table 3, below.

TABLE 3

Analysis of bronchoalveolar lavage fluid at day 14 after the bleomycin administration

| | | Average cell number ± S.D. (×10⁵/ml) | | | | |
|---|---|---|---|---|---|---|
| Group | n | Total cell number | Macrophage | Lymphocyte | Neutrophil | Acidophil |
| Control | 3 | 8.31 ± 1.23 | 5.80 ± 1.23 | 2.26 ± 0.21 | 0.25 ± 0.09 | 0.00 ± 0.00 |
| shFas(nd29)-Fc 50 µg/mouse day 7, i.v. | 4 | 4.80 ± 3.00 | 3.16 ± 1.81 | 1.45 ± 1.09 | 0.19 ± 0.21 | 0.00 ± 0.00 |
| shFas(nd29)-Fc 50 µg/mouse day 10, i.v. | 4 | 2.81 ± 1.84 | 2.26 ± 1.27 | 0.46 ± 0.51 | 0.09 ± 0.12 | 0.00 ± 0.00 |
| shFas(nd29)-Fc 50 µg/ml day 2, 4, 6, 8, 10, and 12 inhalation | 8 | 7.06 ± 7.10 | 5.57 ± 5.51 | 1.20 ± 1.36 | 0.29 ± 0.42 | 0.00 ± 0.00 |
| shFas(nd29)-Fc 50 µg/ml day 2, 4, 6, and 8 inhalation | 4 | 4.51 ± 2.22 | 3.20 ± 1.05 | 1.07 ± 0.88 | 0.17 ± 0.19 | 0.00 ± 0.00 |

(5) Hydroxyproline Assay

The lungs were extirpated at 14 days after the bleomycin administration, and frozen by using liquid nitrogen. The lungs were then minced to a fine homogeneous mixture, and the lung tissue was hydrolyzed in 6N HCl for 16 hours at 120° C. The samples were determined for their hydroxyproline content according to the protocol of Woessner (Arch. Biochem. Biophys., 1961). The results were compared between the groups by using the hydroxyproline content in 1 mg dry lung weight for the index.

The results of the hydroxyproline measurement are shown in Table 4, below.

TABLE 4

Amount of hydroxyproline in lung at day 14 after the bleomycin administration

| Group | n | Amount of hydroxy-proline in 1 mg of lung average ± S.D. (µg/mg) |
|---|---|---|
| Control | 3 | 56.1 ± 6.88 |
| shFas(nd29)-Fc 50 µg/mouse day 7, i.v. | 3 | 14.6 ± 18.1 |
| shFas(nd29)-Fc 50 µg/mouse day 10, i.v. | 3 | 17.2 ± 13.0 |
| shFas(nd29)-Fc 50 µg/ml day 2, 4, 6, 8, 10, and 12, inhalation | 3 | 13.7 ± 20.7 |

(6) Results

The histological analysis demonstrated that the degree of tissue disorder associated with the inflammation or the fibrosis was lighter in the group administered with the shFas(nd29)-Fc compared to the control group.

In the analysis of the cell number in bronchoalveolar lavage fluid, the group administered with shFas(nd29)-Fc exhibited smaller cell number in all or some of the total cell number and the numbers of the macrophage, the lymphocyte, and the neutrophil compared to the control group.

In the measurement of the hydroxyproline content, the group administered with the shFas(nd29)-Fc exhibited lower lung tissue hydroxyproline content than the control group.

Since hydroxyproline is an amino acid specific to the collagen which is an indicator of the fibrotic change, the lung tissue collagen content of the group administered with the shFas(nd29)-Fc was lower than the collagen content of the control group, and the effect of the shFas(nd29)-Fc in suppressing the fibrotic change was thus demonstrated.

EXAMPLE 3

Production of Anti-Mouse Fas Ligand Antibody and its Purification (1) Production of Anti-Mouse Fas Ligand Antibody A plasmid containing human elongation factor (EF) promoter, and in its downstream, the gene coding for the chimeric protein prepared by fusing the extracellular domain of mouse Fas ligand from mouse Fas ligand WX2 (J. Immunology, vol. 157, pages 3918–3924, 1996) and the cytoplasmic domain, the transmembrane domain, and a part of the extracellular domain (from N terminal to 78th amino acid) of mouse CD40 ligand was prepared by genetic engineering means (Mizushima-Nagata, Nucleic Acids Research, vol. 18, page 5322, 1990). The plasmid was transfected in WR19L cell to obtain a recombinant cell W40LFL expressing the mouse Fas ligand on its cell membrane for use as the antigen to be administered. Armenian hamsters were used for the animals to be immunized. The Armenian hamsters were subcutaneously administered with $1 \times 10^7$ W40LFL mixed with Freund complete adjuvant, and a month later, subcutaneously administered with $2 \times 10^7$ W40LFL suspended in PBS, and in another month later, administered with $5 \times 10^6$ W40LFL suspended in PBS from their foot pad. 3 days after the administration, lymph node cells were collected and fused with mouse myeloma cell P3-X63-Ag8-U1 (P3-U1). After selecting the hybridoma by HAT medium (hypoxanthine-aminopterin-thymidine), hybridoma FLIM58 whose supernatant had neutralizing activity for cytotoxicity of mouse Fas ligand was obtained from the survived hybridomas.

(2) Production of FLIM58 and its Purification

Hybridoma FLIM58 was cultivated in serum-free medium Hybridoma-SFM (GIBCO BRL), and the culture supernatant was purified by protein A column (PROSEP-A, Bioprocessing) to obtain purified antibody FLIM58. Concentration of the protein was calculated from absorbance at 280 nm.

EXAMPLE 4

Toxicity Study of the Anti-Mouse Fas Ligand Antibody FLIM58

(1) Method

Male, 8 week old DBA/1J mice and C3H/He mice (Charles River Japan) were used. The mice were administered from their tail vein with the anti-mouse Fas ligand antibody FLIM58 at a dose of 100 mg/30 ml/kg. The control group was administered from their tail vein with physiological saline at a dose of 30 ml/kg. The group consisted three animals for both strains. Observation period was 7 days, and body weight measurement, hematological tests (red blood cell, white blood cell, platelet), and hematobiological tests (GOT, GPT, urea nitrogen), and autopsy with visual inspection were conducted.

(2) Results

The body weight increase, the hematological test values (red blood cell, white blood cell, platelet), and the hematobiological test values (GOT, GPT, urea nitrogen) of the group administered with the anti-mouse Fas ligand antibody FLIM58 were not significantly different from those of the control group. In addition, no abnormalities were found in the group administered with the anti-mouse Fas ligand antibody FLIM58 by the autopsy with visual inspecton.

EXAMPLE 5

Effects of Mouse Fas Ligand Antibody FLIM58 in Ameliorating the Bleomycin-Induced Pulmonary Fibrosis Model Mouse (1) Preparation of Bleomycin-Induced Pulmonary Fibrosis Model Bleomycin-induced pulmonary fibrosis model animals were prepared by repeating the procedure of Example 2 except that the bleomycin chloride (manufactured by Nippon Kayaku) was dissolved in physiological saline to 1 U/kg.

(2) Administration of FLIM58

A group of 4 animals were administered from their tail vein with 100 μg/mouse of FLIM58 on the next day and 7 days after the bleomycin administration (total, 200 μg/mouse), and another group of 10 animals were administered from their tail vein with 200 μg/mouse of FLIM58 after 7 days from the bleomycin administration. A group of control animals were administered only with the bleomycin and no FLIM58.

(3) Histological Evaluation

The animals were histologically evaluated as in the case of Example 2.

The results of the histological evaluation are shown in Table 5.

TABLE 5

Histological Evaluation at day 14 after the bleomycin administration

| Group | Percentage of animals confirmed to have inflammation and fibrosis | | Pathological score |
|---|---|---|---|
| | n | (%) | average ± S.D. |
| Control | 10 | 100 | 2.8 ± 0.4 |
| FLIM58 100 μg/mouse × 2, on day 1 and 7, i.v. | 4 | 25 | 0.8 ± 1.5 |
| FLIM58 200 μg/mouse, on day 7, i.v. | 10 | 50 | 0.9 ± 1.2 |

(4) Results

The histological analysis demonstrated that the degree of tissue disorder associated with the inflammation or the fibrosis was lighter in the group administered with the FLIM58 compared to the control group.

INDUSTRIAL APPLICABILITY

The preventive and therapeutic agent for diffuse lung diseases of the present invention contains an apoptosis-suppressing substance as its effective component. Therefore, it has the action of suppressing the apoptosis, and hence, the effects of preventing or treating the biological actions such as Fas-mediated cell death where Fas/Fas ligand system is involved, and diffuse lung diseases wherein apoptosis is involved. The apoptosis-suppressing substance of the present invention is highly expected for use in prophylactic and therapeutic treatments of the diffuse lung diseases wherein the Fas-mediated cell death and other apoptotic mechanisms are involved.

What is claimed is:

1. A method for treating a disease selected from the group consisting of cryptogenic interstitial pneumonia and pulmonary fibrosis which comprises administering a polypeptide which inhibits Fas-Fas ligand interaction and Fas-mediated apoptosis, wherein said polypeptide is selected from the group consisting of extracellular domain of Fas, a truncated form of the extracellular domain of Fas, a truncated form of a Fas which is deleted in the transmembrane domain, extracellular domain of Fas in which at least one amino acid residue is deleted from the $1^{st}$ to $42^{nd}$ amino acid residues counting from the N-terminus of Fas, and a chimeric protein comprising said polypeptide and an Fc region of an immunoglobulin.

2. A method for treating a disease selected from the group consisting of cryptogenic interstitial pneumonia and pulmonary fibrosis which comprises administering anti-Fas ligand antibody.

3. A method for treating a disease selected from the group consisting of cryptogenic interstitial pneumonia and pulmonary fibrosis which comprises administering humanized anti-Fas ligand antibody.

4. A method for treating a bleomycin-induced diffuse lung disease which comprises administering a polypeptide which inhibits Fas-Fas ligand interaction and Fas-mediated apoptosis, wherein said polypeptide is selected from the group consisting of extracellular domain of Fas, a truncated form of the extracellular domain of Fas, a truncated form of a Fas which is deleted in the transmembrane domain, extracellular domain of Fas in which at least one amino acid residue is deleted from the $1^{st}$ to $42^{nd}$ amino acid residues counting from the N-terminus of Fas, and a chimeric protein comprising said polypeptide and an Fc region of an immunoglobulin.

5. A method for treating a bleomycin-induced diffuse lung disease which comprises administering anti-Fas ligand antibody.

6. A method for treating a bleomycin-induced diffuse lung disease which comprises administering humanized anti-Fas ligand antibody.

* * * * *